(12) United States Patent  
Belhe et al.

(10) Patent No.: US 8,382,794 B2
(45) Date of Patent: Feb. 26, 2013

(54) BALLOON INSERTION APPARATUS AND METHOD OF SEALING A TISSUE PUNCTURE

(75) Inventors: Kedar R. Belhe, Minnetonka, MN (US); Michelle Boucha-Rayle, Minnetonka, MN (US); Catherine A. Pipenhagen, Chanhassen, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 956 days.

(21) Appl. No.: 11/325,206

(22) Filed: Jan. 4, 2006

(65) Prior Publication Data

US 2007/0156084 A1 Jul. 5, 2007

(51) Int. Cl.
A61M 31/00 (2006.01)
(52) U.S. Cl. .......................... 606/213; 606/216
(58) Field of Classification Search .................. 606/191, 606/32, 213–216; 424/422–424; 604/19, 604/22, 500, 506–509
See application file for complete search history.

(56) References Cited

U.S. PATENT DOCUMENTS

| | | | |
|---|---|---|---|
| 4,317,445 A | 3/1982 | Robinson | |
| 4,744,364 A | 5/1988 | Kensey | |
| 4,890,612 A | 1/1990 | Kensey | |
| 5,021,059 A | 6/1991 | Kensey et al. | |
| 5,061,274 A | 10/1991 | Kensey | |
| 5,108,421 A | 4/1992 | Fowler | |
| 5,192,300 A | 3/1993 | Fowler | |
| 5,192,302 A | 3/1993 | Kensey et al. | |
| 5,222,974 A | 6/1993 | Kensey et al. | |
| 5,275,616 A | 1/1994 | Fowler | |
| 5,282,827 A | 2/1994 | Kensey et al. | |
| 5,290,310 A | 3/1994 | Makower et al. | |
| 5,292,332 A | 3/1994 | Lee | |
| 5,304,184 A | 4/1994 | Hathaway et al. | |
| 5,306,254 A | 4/1994 | Nash et al. | |
| 5,312,435 A | 5/1994 | Nash et al. | |
| 5,320,639 A | 6/1994 | Rudnick | |
| 5,326,350 A | 7/1994 | Li | |
| 5,334,216 A | 8/1994 | Vidal et al. | |
| 5,342,393 A | 8/1994 | Stack | |
| 5,368,601 A | 11/1994 | Sauer et al. | |
| 5,383,896 A | 1/1995 | Gershony et al. | |
| 5,383,897 A | 1/1995 | Wholey | |
| 5,383,899 A | 1/1995 | Hammerslag | |
| RE34,866 E | 2/1995 | Kensey et al. | |
| 5,391,183 A | 2/1995 | Janzen et al. | |
| 5,403,328 A | 4/1995 | Shallman | |
| 5,403,329 A | 4/1995 | Hinchcliffe | |
| 5,405,354 A | 4/1995 | Sarrett | |
| 5,411,520 A | 5/1995 | Nash et al. | |
| 5,417,699 A | 5/1995 | Klein et al. | |
| 5,431,639 A | 7/1995 | Shaw | |
| 5,431,666 A | 7/1995 | Sauer et al. | |
| 5,437,631 A | 8/1995 | Janzen | |
| 5,443,481 A | 8/1995 | Lee | |
| 5,462,561 A | 10/1995 | Voda | |
| 5,478,352 A | 12/1995 | Fowler | |
| 5,486,195 A * | 1/1996 | Myers et al. ................. | 606/213 |
| 5,496,332 A | 3/1996 | Sierra et al. | |
| 5,496,335 A | 3/1996 | Thomason et al. | |

(Continued)

*Primary Examiner* — Corrine M McDermott
*Assistant Examiner* — Mark Mashack
(74) *Attorney, Agent, or Firm* — Holland & Hart LLP (57) ABSTRACT

The present invention provides apparatus and methods of closing internal tissue punctures. The apparatus and method provide for an introducer sheath having at least one side port enabling aspiration of an internal tissue puncture site and injection of a sealant.

23 Claims, 6 Drawing Sheets

U.S. PATENT DOCUMENTS

| | | | | |
|---|---|---|---|---|
| 5,507,744 | A | 4/1996 | Tay et al. | |
| 5,507,758 | A | 4/1996 | Thomason et al. | |
| 5,527,322 | A | 6/1996 | Klein et al. | |
| 5,531,759 | A | 7/1996 | Kensey et al. | |
| 5,545,178 | A | 8/1996 | Kensey et al. | |
| 5,549,633 | A | 8/1996 | Evans et al. | |
| 5,554,106 | A | 9/1996 | Layman-Spillar et al. | |
| 5,571,181 | A | 11/1996 | Li | |
| 5,591,205 | A | 1/1997 | Fowler | |
| 5,593,422 | A | 1/1997 | Muijs Van de Moer et al. | |
| 5,601,602 | A | 2/1997 | Fowler | |
| 5,601,603 | A | 2/1997 | Illi | |
| 5,613,974 | A | 3/1997 | Andreas et al. | |
| 5,620,461 | A | 4/1997 | Muijs Van De Moer et al. | |
| 5,626,601 | A | 5/1997 | Gershony et al. | |
| 5,643,318 | A | 7/1997 | Tsukernik et al. | |
| 5,645,566 | A | 7/1997 | Brenneman et al. | |
| 5,649,959 | A | 7/1997 | Hannam et al. | |
| 5,653,730 | A | 8/1997 | Hammerslag | |
| 5,662,681 | A | 9/1997 | Nash et al. | |
| 5,665,106 | A | 9/1997 | Hammerslag | |
| 5,674,231 | A | 10/1997 | Green et al. | |
| 5,676,689 | A | 10/1997 | Kensey et al. | |
| 5,681,334 | A | 10/1997 | Evans et al. | |
| 5,700,277 | A | 12/1997 | Nash et al. | |
| 5,716,375 | A | 2/1998 | Fowler | |
| 5,725,498 | A | 3/1998 | Janzen et al. | |
| 5,725,551 | A | 3/1998 | Myers et al. | |
| 5,728,122 | A | 3/1998 | Leschinsky et al. | |
| 5,728,132 | A | 3/1998 | Van Tassel et al. | |
| 5,728,133 | A | 3/1998 | Kontos | |
| 5,728,134 | A | 3/1998 | Barak | |
| 5,741,223 | A | 4/1998 | Janzen et al. | |
| 5,746,755 | A | 5/1998 | Wood et al. | |
| 5,755,727 | A | 5/1998 | Kontos | |
| 5,759,194 | A | 6/1998 | Hammerslag | |
| 5,766,183 | A | 6/1998 | Sauer | |
| 5,766,206 | A | 6/1998 | Wijkamp et al. | |
| 5,782,861 | A | 7/1998 | Cragg et al. | |
| 5,792,173 | A | 8/1998 | Breen et al. | |
| 5,810,810 | A | 9/1998 | Tay et al. | |
| 5,810,846 | A | 9/1998 | Virnich et al. | |
| 5,810,884 | A | 9/1998 | Kim | |
| 5,814,065 | A | 9/1998 | Diaz | |
| 5,820,631 | A | 10/1998 | Nobles | |
| 5,827,299 | A | 10/1998 | Thomason et al. | |
| 5,830,130 | A | 11/1998 | Janzen et al. | |
| 5,843,124 | A | 12/1998 | Hammerslag | |
| 5,853,421 | A | 12/1998 | Leschinsky et al. | |
| 5,855,559 | A | 1/1999 | Van Tassel et al. | |
| 5,855,585 | A | 1/1999 | Kontos | |
| 5,860,990 | A | 1/1999 | Nobles et al. | |
| 5,861,004 | A | 1/1999 | Kensey et al. | |
| 5,861,005 | A | 1/1999 | Kontos | |
| 5,868,762 | A | 2/1999 | Cragg et al. | |
| 5,868,778 | A | 2/1999 | Gershony et al. | |
| 5,876,411 | A | 3/1999 | Kontos | |
| 5,902,311 | A | 5/1999 | Andreas et al. | |
| 5,906,631 | A | 5/1999 | Imran | |
| 5,910,155 | A | 6/1999 | Ratcliff et al. | |
| 5,919,207 | A | 7/1999 | Taheri | |
| 5,941,897 | A | 8/1999 | Myers | |
| 5,951,583 | A * | 9/1999 | Jensen et al. | 606/194 |
| 5,957,952 | A | 9/1999 | Gershony et al. | |
| 5,964,782 | A | 10/1999 | Lafontaine et al. | |
| 5,976,161 | A | 11/1999 | Kirsch et al. | |
| 5,980,539 | A | 11/1999 | Kontos | |
| 5,997,555 | A | 12/1999 | Kontos | |
| 6,007,562 | A | 12/1999 | Harren et al. | |
| 6,007,563 | A | 12/1999 | Nash et al. | |
| 6,017,359 | A | 1/2000 | Gershony et al. | |
| 6,024,747 | A | 2/2000 | Kontos | |
| 6,033,401 | A | 3/2000 | Edwards et al. | |
| 6,033,427 | A | 3/2000 | Lee | |
| 6,036,721 | A | 3/2000 | Harren et al. | |
| 6,042,601 | A | 3/2000 | Smith | |
| 6,045,569 | A | 4/2000 | Kensey et al. | |
| 6,048,357 | A | 4/2000 | Kontos | |
| 6,048,358 | A | 4/2000 | Barak | |
| 6,063,085 | A | 5/2000 | Tay et al. | |
| 6,071,300 | A | 6/2000 | Brenneman et al. | |
| 6,077,279 | A | 6/2000 | Kontos | |
| 6,090,130 | A | 7/2000 | Nash et al. | |
| 6,110,184 | A | 8/2000 | Weadock | |
| 6,120,524 | A | 9/2000 | Taheri | |
| 6,126,675 | A | 10/2000 | Shchervinsky et al. | |
| 6,136,010 | A | 10/2000 | Modesitt et al. | |
| 6,139,556 | A | 10/2000 | Kontos | |
| 6,162,192 | A | 12/2000 | Cragg et al. | |
| 6,162,240 | A * | 12/2000 | Cates et al. | 606/213 |
| 6,174,322 | B1 | 1/2001 | Schneidt | |
| 6,179,862 | B1 * | 1/2001 | Sawhney | 606/214 |
| 6,179,863 | B1 | 1/2001 | Kensey et al. | |
| 6,183,496 | B1 | 2/2001 | Urbanski | |
| 6,193,670 | B1 | 2/2001 | Van Tassel et al. | |
| 6,197,042 | B1 | 3/2001 | Ginn et al. | |
| 6,206,895 | B1 | 3/2001 | Levinson | |
| 6,231,561 | B1 | 5/2001 | Frazier et al. | |
| 6,245,080 | B1 | 6/2001 | Levinson | |
| 6,296,658 | B1 | 10/2001 | Gershony | |
| 6,398,796 | B2 | 6/2002 | Levinson | |
| 6,425,911 | B1 | 7/2002 | Akerfeldt et al. | |
| 6,425,924 | B1 | 7/2002 | Rousseau | |
| 6,482,223 | B1 * | 11/2002 | Nowakowski et al. | 606/213 |
| 6,508,828 | B1 | 1/2003 | Akerfeldt et al. | |
| 6,547,806 | B1 | 4/2003 | Ding | |
| 6,569,185 | B2 | 5/2003 | Ungs | |
| 6,596,012 | B2 | 7/2003 | Akerfeldt et al. | |
| 6,596,014 | B2 | 7/2003 | Levinson et al. | |
| 6,682,489 | B2 | 1/2004 | Tenerz et al. | |
| 6,712,837 | B2 | 3/2004 | Akerfeldt et al. | |
| 6,743,195 | B2 | 6/2004 | Zucker | |
| 6,860,895 | B1 | 3/2005 | Akerfeldt et al. | |
| 6,929,655 | B2 | 8/2005 | Egnelov et al. | |
| 2004/0172058 | A1 * | 9/2004 | Edwards et al. | 606/213 |
| 2004/0249342 | A1 * | 12/2004 | Khosravi et al. | 604/96.01 |
| 2005/0107826 | A1 * | 5/2005 | Zhu et al. | 606/213 |
| 2005/0149117 | A1 * | 7/2005 | Khosravi et al. | 606/215 |
| 2005/0228443 | A1 | 10/2005 | Yassinzadeh | |
| 2007/0156084 | A1 | 7/2007 | Belhe et al. | |

* cited by examiner

BALLOON INSERTION APPARATUS AND METHOD OF SEALING A TISSUE PUNCTURE

FIELD OF THE INVENTION

The present invention relates to medical devices, and, more particularly, to tissue puncture sealing devices.

BACKGROUND OF THE INVENTION

Various medical procedures, particularly cardiology procedures, involve accessing a corporeal vessel or other lumen through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

Historically, the access hole is closed by the application of prolonged manual pressure over the puncture site by a physician or other trained medical professional. The time involved with this method is extensive and costly. In addition, because patients are often treated with a variety of anticoagulant and thrombolytic agents, the manual pressure required to close the access opening in the vessel wall may be even longer. The discomfort and delay in mobilization for patients resulting from this prolonged manual pressure is significant.

Therefore, a number of vascular closure devices have been developed to close an access opening in the vessel wall more efficiently. For example, closing an access opening in the vessel wall may involve packing a resorbable sealing plug at the hole or sandwiching the hole between the sealing plug and an anchor. Examples of such vascular closure devices and methods are described in U.S. Pat. Nos. 6,179,863; 6,090,130; and 6,045,569 and related patents that are hereby incorporated by reference.

Alternatively, closing an access opening in the vessel wall may include the use of a balloon catheter. For example, an access opening in the vessel wall may be closed by inserting a balloon catheter through the opening in the vessel wall, inflating the balloon, pulling the balloon against the inner wall of the vessel, introducing a procoagulant to the incision site external to the puncture in the vessel wall, and withdrawing the balloon catheter. This method relies on a biochemical reaction between the procoagulant and the blood. The reliance on a biochemical reaction, however, can be problematic. For example, the mixing of the procoagulant with the blood is arbitrary. Therefore, in many cases an exaggerated dose of the procoagulant is applied in an attempt to ensure hemostatis. An exaggerated dose, however, can accidentally enter the blood stream and introduce complications. Moreover, reliance on a chemical reaction based on arbitrary mixing between the procoagulant and the blood often results in an inconsistent seal composition, which in turn results in inconsistent hemostatic sealing performance.

SUMMARY OF THE INVENTION

In one of many possible embodiments, the present invention provides an internal tissue puncture sealing apparatus. The internal tissue puncture sealing apparatus comprises a first thin, elongated conduit having a first central lumen and first and second ends. The first end is insertable through the internal tissue puncture and has an inflation segment in fluid communication with the central lumen. The first end includes an expandable member that is selectively inflatable with a fluid via the central lumen. The apparatus also includes a second thin, elongated conduit having a second central lumen receptive of the first thin, elongated conduit. The proximal end of the second conduit has at least one valved side-port in fluid communication with an annulus between the first and second conduits. The valved side-port may include a vacuum communication path and a sealant injection path, which enable aspiration of a tissue puncture site and sealing of the puncture.

Another aspect of the invention provides a method of closing a hole in a vessel wall. The method may include inserting an inflatable device through an introducer that is disposed in the vessel, inflating the inflatable device, sealing the inflatable device against an inner wall of the vessel, reducing the pressure inside of the introducer, injecting a sealant into the introducer, deflating the inflatable device, and removing the inflatable device through the sealant. Following removal of the inflatable device, manual pressure may be applied to the hole for a short period of time to ensure continued hemostasis. According to some aspects of the invention, a specially designed introducer is swapped with a standard introducer used to facilitate insertion of vascular tools used to perform a vascular procedure prior to inserting the inflatable device.

The foregoing and other features, utilities and advantages of the invention will be apparent from the following more particular description of preferred embodiments of the invention as illustrated in the accompanying drawings.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

As mentioned above, vascular procedures are commonly performed throughout the world and require access to a blood vessel through a puncture or opening in the vessel. Often an introducer sheath is placed in the opening to facilitate access to the vessel by one or more vascular instruments, including puncture closure devices. Proper location of an artery or other lumen is typically indicated by a flow of blood through the lumen into the introducer sheath or other instrument as the instrument enters the vessel. The present invention describes methods and apparatus for sealing the vessel opening or arteriotomy following completion of a vascular procedure. The methods and apparatus may also be used, however, to close punctures caused by accidents or other injuries, and are not limited to use following a vascular procedure. The principles described herein may be used to close internal tissue punctures of any kind in any live body. Therefore, while the description below is directed primarily to closing arteriotomys, the methods and apparatus may be used according to principles described herein with any bodily lumen to close a hole or puncture.

As used throughout the claims and specification, the term "sealant" is used broadly to encompass any fluid, foam, or gel that does not require a biochemical reaction with bodily fluids to set or cure for sealing purposes. The term "fluid" refers to molecules of a substance that move freely past one another and have the tendency to assume the shape of its container, including liquids, foams, gels, and gasses. A "lumen" refers to any open space or cavity in a bodily organ, especially in a blood vessel, or a fluid passageway through a vascular device. "Aspirate" or "aspirating" means to remove fluids with a suction device. The term "vacuum" means lower pressure than local atmospheric pressure or a device that creates a lower pressure. The words "having" and "including" have the same meaning as the word "comprising."

Figure 1:
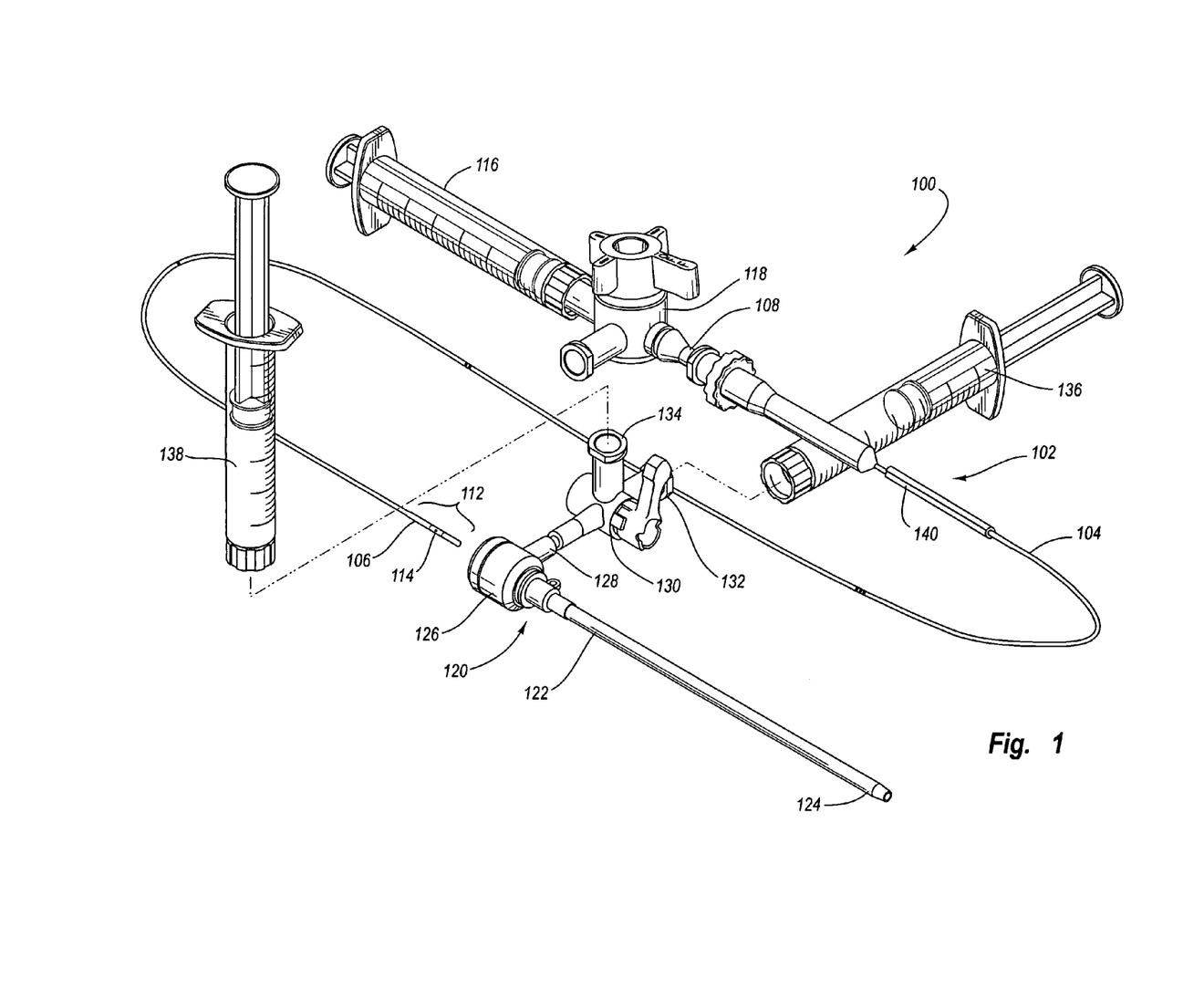
FIG. 1 is an exploded assembly view of an introducer sheath and an associated balloon catheter according to one embodiment of the present invention.

Referring now to the drawings, and in particular to FIG. 1, an internal tissue puncture sealing apparatus 100 according to one embodiment of the present invention is shown. As shown in FIG. 1, the internal tissue puncture sealing apparatus 100 includes a first thin, elongated conduit. According to FIG. 1, the first thin, elongated conduit is a balloon catheter 102 and includes a first central lumen 104 and first and second ends 106, 108, respectively. The first end 106 includes an inflation segment 112. According to FIG. 1, the inflation segment 112 comprises an expandable member such as a balloon 114 that is in fluid communication with the central lumen 104. Therefore, the balloon 114 is selectively inflatable with a fluid via the central lumen 104. The balloon 114 may be inflated by increasing the pressure of the fluid inside the central lumen 104. For example, the second end 108 of the balloon catheter includes a syringe 116 that may be depressed to inflate the balloon 114 with saline solution. Downstream of the syringe 116 is a valve 118 that selectively isolates the central lumen 104 from the syringe 116. Accordingly, when the valve 118 is open, the syringe 116 may be depressed, resulting in expansion or inflation of the balloon 114. Further, following inflation, the valve 118 may be closed, maintaining the expansion of the balloon 114. When uninflated as shown in FIG. 1, the balloon 114 is coaxial and substantially flush with the central lumen 104.

The internal tissue puncture sealing apparatus 100 also includes a second thin, elongated conduit. According to FIG. 1, the second thin, elongated conduit comprises an introducer assembly or sheath 120. The introducer sheath 120 has a second central lumen 122 that is receptive of the balloon catheter 102.

The introducer sheath 120 also has a distal end 124 and a proximal end 126. The proximal end 126 includes at least one side-port 128 extending into the second central lumen 122. According to FIG. 1, the side-port 128 is in fluid communication with an external valve 130. The external valve 130 branches to a vacuum port 132 and a sealant injection port 134. However, according to some embodiments the vacuum port 132 and sealant injection port 134 are one and the same, and thus there may be no branching.

As shown in FIG. 1, the vacuum port 132 is in fluid communication with a vacuum source or other evacuator, for example a vacuum syringe 136. Similarly, the sealant injection port 134 is in fluid communication with a sealant supply, such as a sealant-containing syringe 138. Therefore, the external valve 130 may comprise a translucent three-way valve positionable between a first or closed position isolating both the vacuum port 132 and the sealant injection port 134 from the second central lumen 122, a second position opening a fluid communication path between the second central lumen 122 and the vacuum port 132, and a third position opening a fluid communication path between the second central lumen 122 and the sealant injection port 134. Details of the external valve 130 and the associated vacuum port 132 and sealant injection port 134 are shown in FIGS. 3-7.

Figure 2:
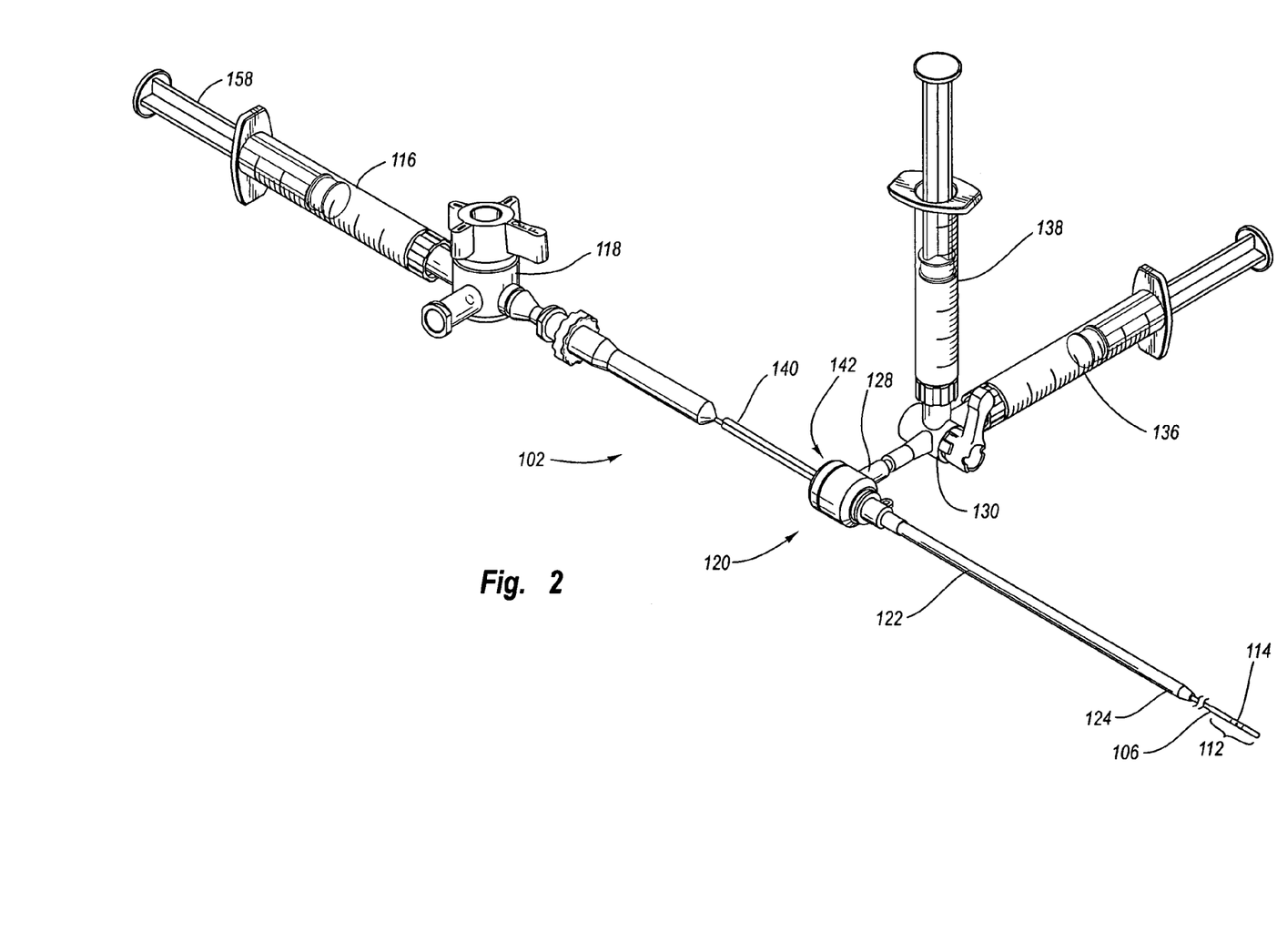
FIG. 2 is a perspective view of the balloon catheter inserted into the introducer sheath.

The balloon catheter 102 may be inserted into the introducer sheath 120 as shown in FIG. 2. When the balloon catheter 102 is inserted into the introducer sheath 120, an annulus 142 is created between the balloon catheter 102 and the introducer sheath 120. The side-port 128 is thus in fluid communication with the annulus 142.

A stopper sleeve or spacer 140 is shown disposed over the balloon catheter 102 to limit the insertion distance of the balloon catheter into the introducer sheath 120. The length of the spacer 140 is chosen such that the first end 106 of the balloon catheter 102 extends beyond the distal end 124 of the introducer sheath 120 by a predetermined distance. According to some embodiments, the predetermined distances is approximately 2.5-4.0 cm. The predetermined distance allows for the balloon 114 of the inflation segment 112 to pass into a vessel as discussed in more detail below. The spacer 140 may comprise a split tube that can be easily removed as desired.

Figures 3, 4:
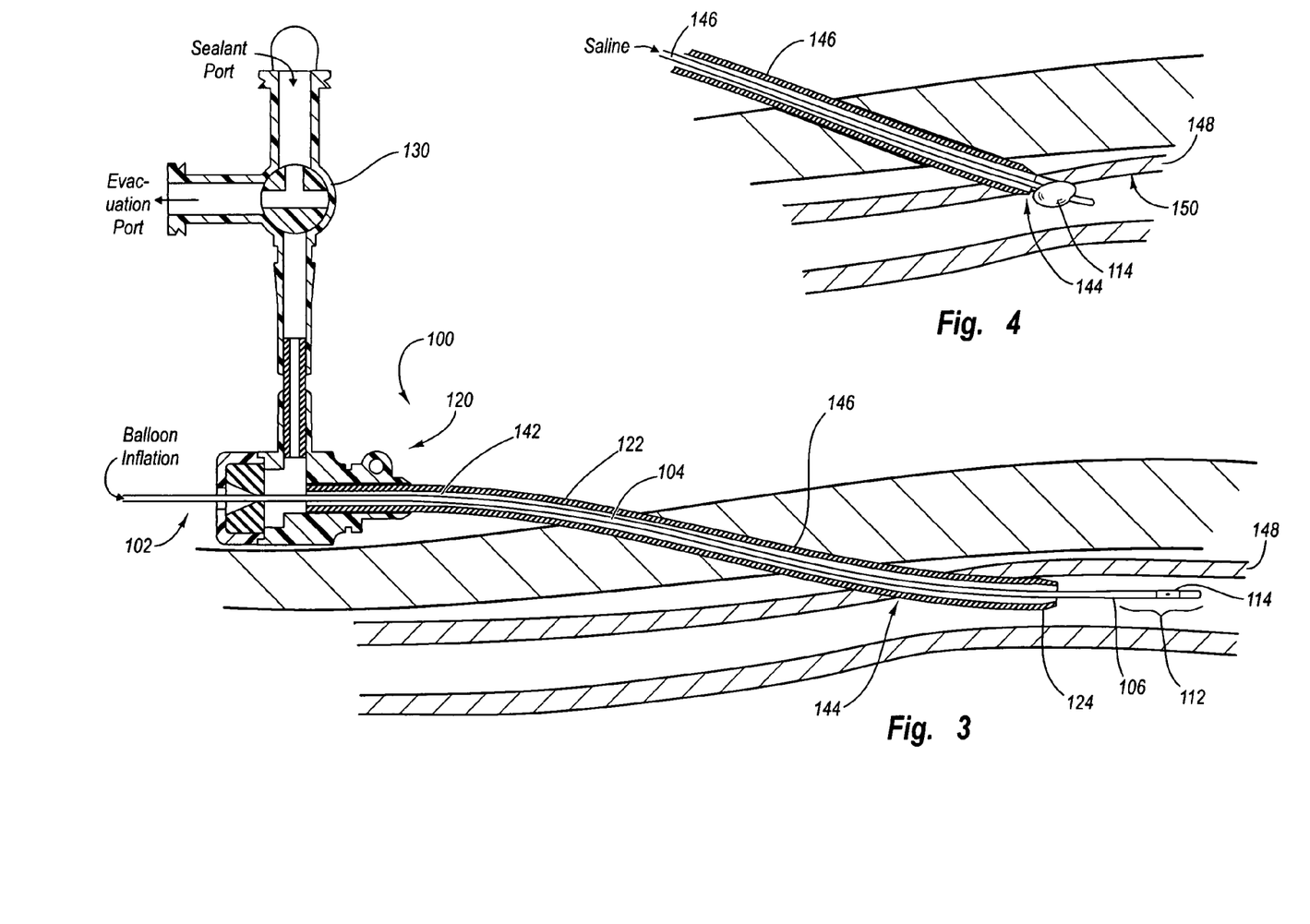
FIG. 3 is a sectional side elevation view of a patient with the introducer sheath of FIG. 1 in place within an arteriotomy and the associated balloon catheter extending through the introducer sheath and into a blood vessel according to one embodiment of the present invention.
FIG. 4 is a sectional side elevation view of the patient, introducer sheath, and balloon catheter of FIG. 3 with a balloon of the balloon catheter inflated and sealing the arteriotomy.

Methods of closing a hole or puncture such as an arteriotomy 144 using the internal tissues puncture sealing apparatus 100 are next discussed with reference to FIGS. 3-8. Referring first to FIG. 3, the tissue puncture sealing apparatus 100 is shown with the introducer sheath 120 inserted into the arteriotomy 144. Although FIG. 3 shows the introducer sheath 120 passing through an incision tract 146 leading to the arteriotomy 144, according to some methods the introducer sheath 120 may be swapped with a standard introducer that may have been used to perform a vascular procedure. Preferably, however, the introducer sheath 120 is used both for introducing instruments used to perform a vascular procedure and for closing the arteriotomy 144.

With the introducer sheath 120 inserted into the arteriotomy, the balloon catheter 102 is introduced through the second central lumen 122 until the first or distal end 106 of the balloon catheter 102, including the inflation segment 112, extends beyond the distal tip 124 of the introducer sheath 120 and into a blood vessel 148. The balloon 114 is in fluid communication with the first central lumen 104. Therefore, opening the catheter valve 118 (FIG. 2) and depressing the syringe 116 (FIG. 2) inflates the balloon 114 of the inflation segment 112 as shown in FIG. 4. To maintain the balloon 114 in an inflated posture, the catheter valve 118 may be closed. The balloon catheter 102 and the introducer sheath 120 are retracted until the balloon 114 bears against an inner wall 150 of the blood vessel 148 and seals the internal portion of the arteriotomy 144 as shown in FIG. 4.

Figure 5:
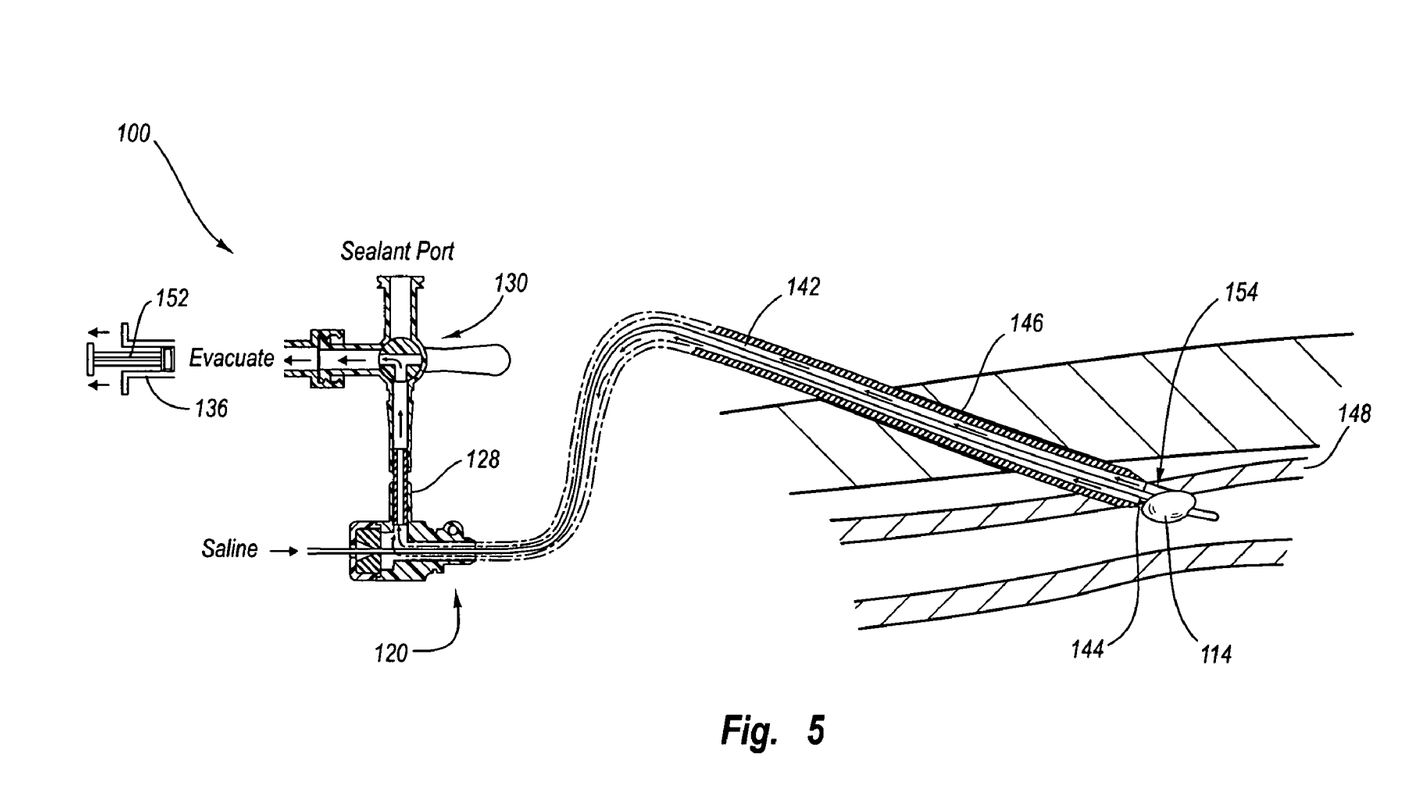
FIG. 5 is a sectional side elevation view of the patient, introducer sheath, and balloon catheter of FIG. 4 shown with the introducer sheath connected to a vacuum apparatus according to one embodiment of the present invention.

With the balloon 114 in place internally sealing the arteriotomy 144, the side-port valve 130 is opened to allow fluid communication between the annulus 142 and the vacuum syringe 136 as shown in FIG. 5. A vacuum is created in the annulus 142 by a withdrawing a stem 152 of the vacuum syringe 136 or by some other vacuum device. As the vacuum is created in the annulus 142 and communicated to the incision tract 146, a situs 154 of the arteriotomy 144 and is aspirated, removing fluids from the incision tract 146 via the annulus 142.

As the arteriotomy 144 is aspirated, a surgeon or other medical professional may visually inspect the fluid contents evacuated through the translucent valve 130 to assess blood flow through the arteriotomy and thereby ensure proper positioning of the introducer sheath 120 and/or the balloon 114 within the blood vessel 148. A flow of blood may indicate that the balloon 114 is not properly sealing the arteriotomy 144.

Figure 6:
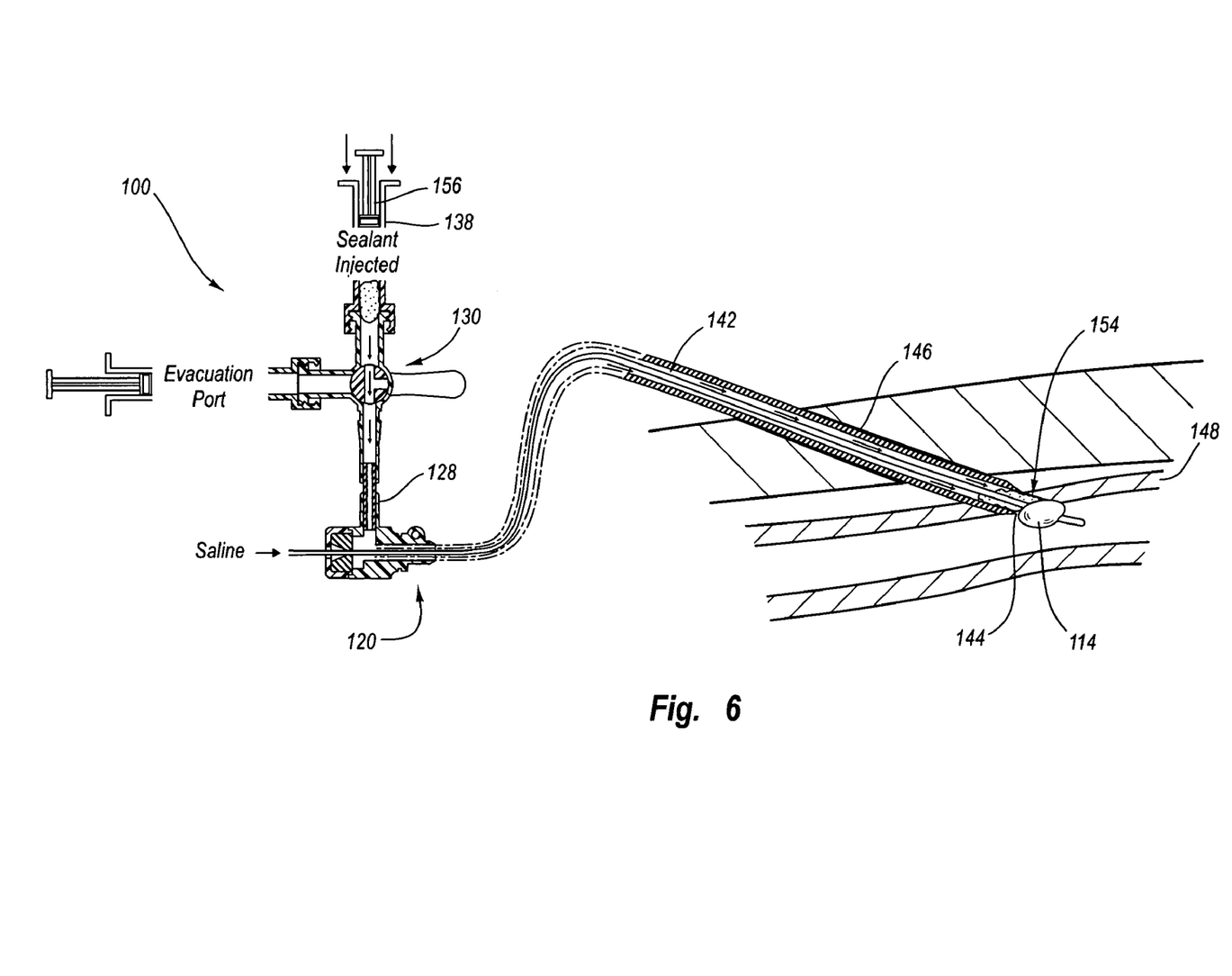
FIG. 6 is a sectional side elevation view of the patient, introducer sheath, and balloon catheter of FIG. 5 shown with the introducer sheath connected to a sealant injector according to one embodiment of the present invention.

When the surgeon is satisfied with the positioning of the introducer sheath 120 and the balloon 114, the side-port valve 130 is toggled to create a fluid communication path between the annulus 142 and the sealant contained by the sealant-containing syringe 138 or other sealant supply as shown in FIG. 6. The sealant-containing syringe 138 holds a volume of sealant that is injected into the introducer sheath 120 via the side-port 128 as a stem 156 is depressed. As shown in FIGS. 5 and 6, the side-port 128 provides a single, common access point for supplying the sealant and vacuum condition to the annulus 142. The sealant flows through the annulus 142 and into the incision tract 146. Further, because the incision tract 146 has been evacuated and is in a vacuum condition, the sealant is drawn through the annulus 142 toward the arteriotomy 144. The vacuum condition of the situs 154 external to the arteriotomy 144 causes the sealant to quickly and efficiently fill all of the voids around the arteriotomy 144 and in the incision tract 146. Preferably, the sealing-containing syringe 138 holds a volume of sealant sufficient to fill the annulus 142 and therefore the incision tract 146. As the sealant is injected, the sheath 120 is preferably withdrawn with respect to the balloon 114 to allow the sealant to fill the incision tract 146. Therefore, in order to facilitate retraction of the sheath 120, the spacer 140 (FIG. 2) is removed.

Following injection of the sealant, the sealant may be optionally activated, cured, or set. The sealant may comprise a gel or foam made of materials including, but not limited to: collagen, polyvinyl alcohol, polyethylene glycol, cyanoacrylates, chitosan, poly-n-acetyl glucosamine. Unlike the materials used in previous devices, none of the materials recited herein is dependent on a biochemical reaction with blood or other bodily fluids to create a hemostatic seal. However, the gels or foams used according to some aspects of the present invention may in some cases be activated or cured by, for example, application of a second fluid, UV light, or other activation mechanisms.

Figure 7:
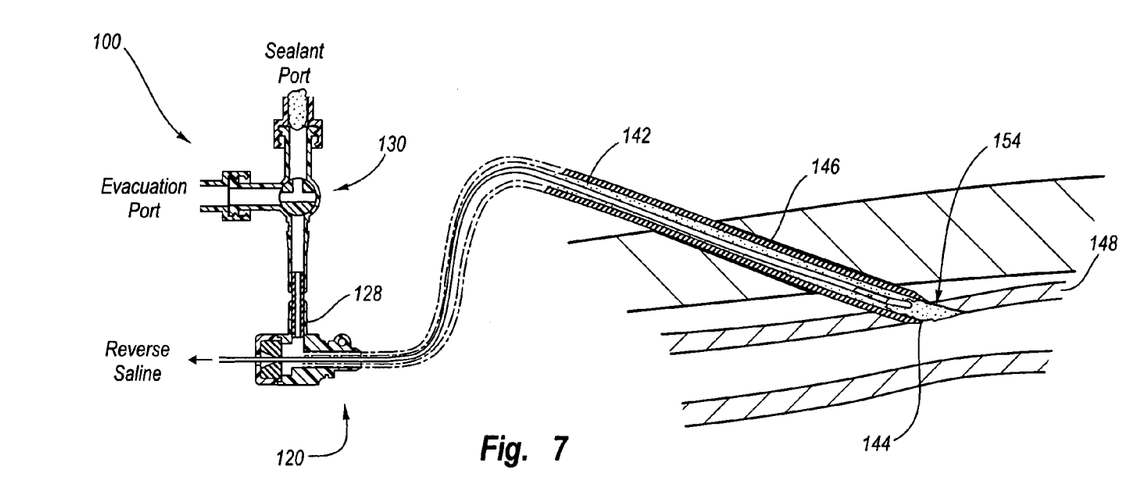
FIG. 7 a sectional side elevation view of the patient, introducer sheath, and balloon catheter of FIG. 6 with the balloon deflated and being withdrawn through the sealant according to one embodiment of the present invention.
Figure 8:
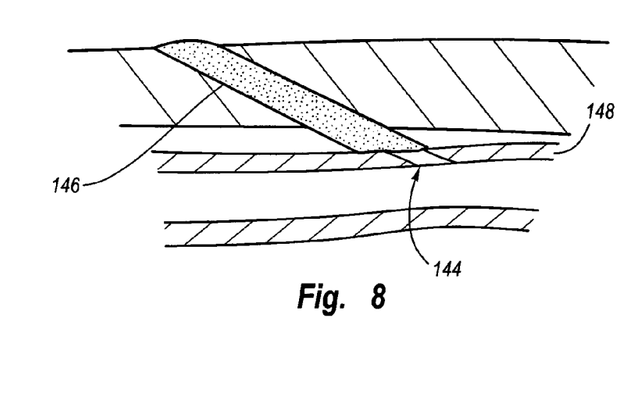
FIG. 8 is a sectional side elevation view of the patient following retraction of the introducer sheath and balloon catheter from the situs of the arteriotomy.

When the sealant is in place adjacent the exterior of the arteriotomy 144, the balloon 114 is deflated as shown in FIG. 7. The balloon 114 is deflated by reopening the catheter valve 118 (FIG. 2). The stem 158 (FIG. 2) of the catheter syringe 116 (FIG. 2) may be retracted to ensure full deflation of the balloon 114. The balloon catheter 102 and the introducer sheath 120 are retracted, with the balloon 114 sliding through the sealant and in contact with the sealant while at least a portion of the sealant remains positioned in and in contact with the introducer sheath 120 as shown in FIG. 7. According to some embodiments, following removal of the balloon catheter and the introducer sheath 120, manual pressure may be applied to the arteriotomy site to counteract any sealing action disruption caused by the act of pulling the balloon 114 through the sealant. However, the manual pressure is applied for only a fraction of the time allocated to traditional arteriotomy closures. For example, according the principles described herein, manual pressure may be applied following retraction of the internal tissue puncture sealing apparatus 100 for only ten minutes or less. The sealant remains in the incision tract 146 sealing the arteriotomy 144 as shown in FIG. 8.

While the invention has been particularly shown and described with reference to embodiments thereof, it will be understood by those skilled in the art that various other changes in the form and details may be made without departing from the scope of the invention.

What is claimed is:

1. A method of closing a hole in a vessel of a patient, comprising:
   inserting an inflatable device through an introducer that is disposed in the blood vessel;
   inflating the inflatable device;
   sealing the inflatable device against an inner wall of a vessel;
   reducing the pressure inside of a lumen of the introducer;
   injecting a sealant into the introducer through the same lumen of the introducer in which the pressure is reduced, the sealant being in direct contact with the introducer, the sealant being drawn toward the hole in the vessel by the reduced pressure inside the introducer, the reduced pressure and sealant being supplied to the lumen at a common access point;
   deflating the inflatable device;
   removing the inflatable device through the sealant while a portion of the sealant is positioned in the introducer.

2. A method of closing a hole in a vessel according to claim 1, further comprising applying manual pressure to the hole following the removing of the inflatable device through the sealant.

3. A method of closing a hole in a vessel according to claim 1 wherein the sealing further comprises withdrawing the inflatable device and the introducer in a direction away from the patient.

4. A method of closing a hole in a vessel according to claim 1 wherein the reducing further comprises evacuating fluids from the introducer and a hole tract.

5. A method of closing a hole in a vessel according to claim 1 wherein the reducing further comprises checking for leaks through the hole by watching for blood flow through the introducer.

6. A method of closing a hole in a vessel according to claim 1 wherein the reducing comprises aspirating a situs of the hole by retracting a syringe connected to the introducer via a side port.

7. A method of closing a hole in a vessel according to claim 1 wherein the sealant comprises an independent gel or foam that is not reliant on a biochemical reaction with blood to create a seal.

8. A method of closing a hole in a vessel according to claim 1 wherein the sealant comprises a gel or foam made from one of: collagen, polyvinyl alcohol, polyethylene glycol, cyanoacrylates, chitosan, or poly-n-acetyl glucosamine.

9. A method of closing a hole in a vessel according to claim 1 wherein the injecting comprises depressing a syringe connected to the introducer via a side port.

10. A method of closing a hole in a vessel according to claim 1, further comprising curing the sealant.

11. A method of sealing an internal tissue puncture, comprising:
   passing a tip of a balloon catheter through a lumen positioned in the internal tissue puncture and into the internal tissue puncture;
   inflating a balloon of the balloon catheter;
   retracting the balloon catheter such that the balloon bears against the internal tissue puncture;
   creating a vacuum in the lumen and applying the vacuum at an external situs of the internal tissue puncture;
   injecting a sealant through the lumen to the external situs, the sealant being in direct contact with the lumen, the sealant being drawn toward the internal tissue puncture by the vacuum, the vacuum and sealant being supplied to the lumen at a common access point;
   deflating the balloon;
   removing the tip of the balloon catheter from the internal tissue puncture and through the sealant while at least a portion of the sealant is positioned in the lumen.

12. A method of sealing an internal tissue puncture according to claim 11, further comprising curing the sealant.

13. A method of sealing an internal tissue puncture according to claim 11, further comprising inserting the balloon catheter through an introducer disposed in the internal tissue puncture, the introducer defining the lumen.

14. A method of sealing an internal tissue puncture according to claim 11, further comprising applying manual pressure to the internal tissue puncture following the removing of the tip of the balloon catheter from the internal tissue puncture for less than ten minutes.

15. A method of sealing an internal tissue puncture according to claim 11 wherein the creating a vacuum further comprises evacuating fluids from an incision tract leading to the internal tissue puncture.

16. A method of sealing an internal tissue puncture according to claim 11 wherein the sealant comprises a gel or foam made from one of: collagen, polyvinyl alcohol, polyethylene glycol, cyanoacrylates, chitosan, or poly-n-acetyl glucosamine.

17. A method of closing an arteriotomy comprising:
   inserting an introducer sheath comprising a valved side-port into the arteriotomy;
   introducing a balloon catheter through the introducer sheath until a distal balloon end of the balloon catheter extends beyond a distal tip of the introducer sheath and into a blood vessel,
   inflating a balloon of the distal balloon end;
   retracting the balloon catheter and introducer sheath until the balloon seals against an internal portion of the arteriotomy;
   creating a vacuum in a lumen of the introducer sheath;
   injecting a volume of sealant into the same lumen of the introducer sheath in which the vacuum is created, the sealant being in direct contact with the introducer sheath, the sealant being drawn toward the arteriotomy by the vacuum, the vacuum and sealant being supplied to the lumen at a common access point;
   deflating the balloon;
   retracting the balloon catheter from the arteriotomy and through the sealant while at least a portion of the sealant is positioned in the introducer sheath.

18. A method of closing an arteriotomy according to claim 17 wherein the inserting further comprises visually assessing blood flow through the side-port to ensure proper positioning of the introducer sheath within the blood vessel.

19. A method of closing an arteriotomy according to claim 17 wherein the creating a vacuum further comprises visually inspecting the side-port for indication of blood flow through the arteriotomy.

20. A method of closing an arteriotomy according to claim 17 wherein the creating a vacuum further comprises aspirating contents of the introducer sheath through the side-port.

21. A method of closing an arteriotomy according to claim 17 wherein the injecting further comprises substantially filling the introducer sheath with and adding a deposit around an exterior of the arteriotomy with the sealant.

22. A method of closing an arteriotomy comprising:
   swapping a standard vascular introducer sheath inserted into a patient with second introducer sheath comprising a valved side-port;
   introducing a balloon catheter through the second introducer sheath until a distal balloon end of the balloon catheter extends beyond a distal tip of the second introducer sheath and into a blood vessel,
   inflating a balloon of the distal balloon end;
   retracting the balloon catheter and second introducer sheath until the balloon seals against an internal portion of the arteriotomy;
   creating a vacuum in a lumen of the second introducer sheath;
   injecting a volume of sealant into the same lumen of the second introducer sheath in which the vacuum is created, the sealant being in direct contact with the second introducer sheath, the sealant being drawn toward the arteriotomy by the vacuum, the vacuum and sealant being supplied to the lumen at a common access point;
   deflating the balloon;
   retracting the balloon catheter from the arteriotomy and through the sealant while at least a portion of the sealant is positioned in the second introducer sheath.

23. A method of closing an arteriotomy according to claim 22 wherein the balloon contacts the sealant while retracting the balloon catheter.

* * * * *